United States Patent [19]
Joslyn

[11] 4,410,493
[45] Oct. 18, 1983

[54] INDICATOR DEVICE FOR USE IN STEAM STERILIZATION

[75] Inventor: Larry J. Joslyn, Macedon, N.Y.

[73] Assignee: Sybron Corporation, Rochester, N.Y.

[21] Appl. No.: 262,497

[22] Filed: May 11, 1981

[51] Int. Cl.³ ............................................. G01N 31/22
[52] U.S. Cl. ..................................... 422/58; 116/219; 422/56; 426/88
[58] Field of Search .................... 422/56, 58; 116/219; 426/88

[56] References Cited

U.S. PATENT DOCUMENTS

| | | |
|---|---|---|
| 2,799,167 | 7/1957 | Loconti . |
| 2,889,799 | 6/1959 | Korpman . |
| 3,002,385 | 10/1961 | Wahl . |
| 3,046,786 | 7/1962 | Tessem . |
| 3,082,624 | 3/1963 | Renier . |
| 3,324,723 | 6/1967 | Ritchie . |
| 3,420,205 | 1/1969 | Morison . |
| 3,479,877 | 11/1969 | Allen . |
| 3,523,011 | 8/1970 | Bhiwandker . |
| 3,932,134 | 1/1976 | Fang . |
| 3,942,467 | 3/1976 | Witonsky . |
| 3,946,611 | 3/1976 | Larsson . |
| 3,946,612 | 3/1976 | Sagi . |
| 3,966,414 | 6/1976 | Khattab . |
| 3,980,581 | 9/1976 | Godsey . |
| 3,981,683 | 9/1976 | Larsson . |
| 3,996,007 | 12/1976 | Fang . |
| 4,042,336 | 8/1977 | Larsson . |
| 4,154,107 | 5/1979 | Giezen . |
| 4,333,339 | 6/1982 | McNeely ...................... 116/219 X |

FOREIGN PATENT DOCUMENTS 889573  2/1962  United Kingdom .

OTHER PUBLICATIONS

D. E. Simpkins et al., J. Pharm. Pharmacol., 1964, 16, Suppl. 108T-110T.
The Lancet, Saturday, Feb. 28, 1959, pp. 425-435.

Primary Examiner—Sidney Marantz
Attorney, Agent, or Firm—Robert A. Gerlach; Owen D. Marjama

[57] ABSTRACT

An indicator device which comprises a backing member, an indicator chemical, such as sebacic acid, which has the capability of wicking through a wick material, wicking means having one end of said wicking means in physical contact with said indicator chemical, said indicator chemical and wicking means being contained within a polypropylene envelope with the top and bottom interfaces of said envelope being sealed together to mechanically bond the wicking means and indicator chemical at the film envelope interfaces.

5 Claims, 5 Drawing Figures

INDICATOR DEVICE FOR USE IN STEAM STERILIZATION

BACKGROUND

Various types of process or chemical indicators are used to measure the concentration of constituents in a liquid or gas environment or to determine the effectiveness of a process under certain environmental conditions. The present invention relates to such process indicators which use permeation or wicking of a substance through a material to react or otherwise cause an indication/measurement of physical condition.

Typical examples of such indicators are illustrated in U.S. Pat. Nos. 3,981,683, 3,932,134, and 4,195,055, which are incorporated herein by reference. Flexible packaging of these indicator devices guides the indicating substance to the barrier or wick. A problem associated with these flexible package indicators, is that changes in environmental conditions, such as temperature and pressure, can cause local deformation of the packaging surrounding the permeation barrier or wick material. As a result, wicking or gas permeation may not be through the specially designed wick or permeable barrier as intended, but through an interspace formed between the wick or barrier and the flexible envelope which forms part of the device. When this occurs, the observer will, of course, receive an erroneous reading which is not related to its exposure.

The present invention is directed to preventing erroneous indications of wicking or permeation indicators by providing a structure which insures that the diffusion or wicking action occurs specifically through the wick or permeation material.

SUMMARY OF THE INVENTION

The present invention is directed to an indicator device which contains a wicking means or permeation barrier. For the purposes of simplicity, where the term wick is used in the specification in a broad or generic sense, it shall also mean or include a permeation path.

The wicking means itself may be treated to provide an indication, such as a color change when exposed to certain constituents in an environment or the wicking means may be wicked by being in contact with an indicating chemical. In order to overcome the problem of secondary wicking which may not be through the wick, but through an interspace formed between the wick and the flexible envelope which generally covers the wick of prior art devices, the present invention employs a specially designed envelope. The wick is sealed, both top and bottom between two layers of film material which is impermeable to the indicator material or medium. The top film and bottom film are sealed together with an adhesive material or heat sealed together at the top and bottom film interface. The adhesive or heat seal not only bonds the top and bottom films to form an envelope, but also bonds the top and bottom of the wick to the top and botton films. This physical bond between the wick and the film interfaces prevents separation of the film from the wick during pressure or temperature excursions which might occur in test environments. Thus any constituent which is to react with the wick must contact the wick at one end and permeate longitudinally through the wick. The constituent reacts with the wick, as a function of time, temperature, and concentration, with progressive migration distance down the wick related to a measurement of the exposure without including false permeation along the periphery of the wick.

DETAILED DESCRIPTION OF THE DRAWINGS

Figure 1:
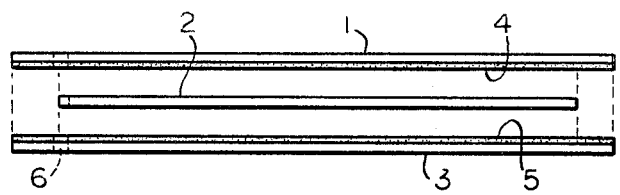
FIGS. 1 and 2 show one embodiment of the indicator device.
Figure 2:
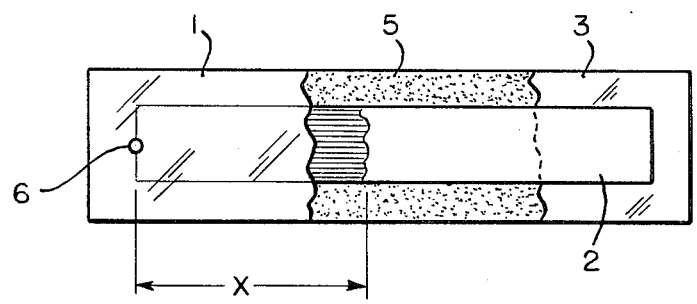

One embodiment of the present invention is illustrated by FIGS. 1 and 2. The structure of an indicator assembly for monitoring constituents in a liquid or gas environment, according to the present invention, consists of a permeable wick material 2 which is treated to provide an indication, such as a color change, when exposed to certain constituents in an environment. The permeable material is sealed between film materials 1 and 3, which are impermeable to the environmental chemicals, except for a hole 6 in one end of the resultant envelope, as shown in FIGS. 1 and 2. The top film 1 and the bottom film 3 are sealed together with an adhesive material or heat sealed together at the top and bottom film interfaces 4 and 5 as illustrated in FIG. 1. The adhesive or heat seal not only bonds the top 1 and bottom 3 film to form an envelope, but also mechanically bonds the top and bottom films to the treated permeable wick material 2. This physical bond between the permeation wick 2 and the film interfaces 4 and 5 prevents separation of the films 1 and 3 from the permeable wick 2 during pressure or temperature excursions which might occur in test environments. Thus, any constituent which is to react with the treated permeable wick 2 must enter through hole 6 and permeate longitudinally through the wick. As the constituent reacts with the treated wick, as a function of time, temperature and concentration, progressive migration down the wick migration distance x can be related to a measurement of the constituent concentration without having false permeation along the periphery of the treated wick 2.

Figure 3:
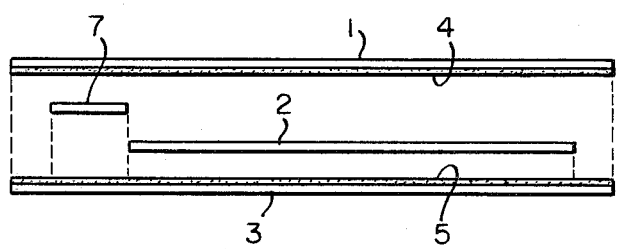
FIGS. 3 and 4 show a second embodiment of the indicator device.
Figure 4:
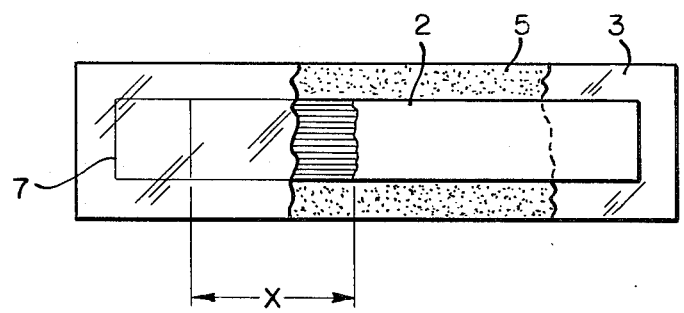

A second embodiment of the present invention is illustrated in FIGS. 3 and 4. This indicator is based upon the rate of an indicating chemical 7 wicking through a wick material 2. The rate of wicking is a function of indicating chemical viscosity, indicating chemical surface tension, wettability of wick by chemical and the mean capillary size of the wick. The present invention prevents the formation of a gap between the top or bottom film 1 and 3 and the wick material 2, which would cause an alternate capillary wicking path, by mechanically bonding the top and bottom film to the wick material at the film interfaces 4 and 5. Thus, under changing environmental conditions, such as temperature and/or pressure, the chemical must wick through the wick material with no false migration along the periphery of the wick material.

Figure 5:
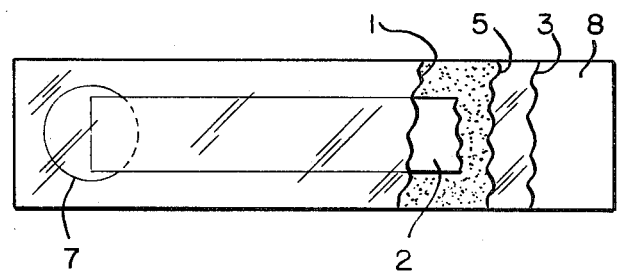
FIG. 5 shows a third embodiment of the indicator device.

In a further embodiment of the present invention, the device of the present invention may be mounted on a suitable backing member 8 as illustrated in FIG. 5.

The wick 2 may comprise any suitable material such as commercially available filter papers known as Whatman 1 or No. 54 or Green's No. 406.

The film material may comprise any suitable plastic such as mylar, polypropylene, polystyrene, polyethylene, etc. The film material should be transparent and should be impermeable and resistant to the chemical or indicator medium which will react with the wick. It should be understood that the film material may be chosen to be selective to the environment in which it is used. For example, when the indicator is of the type illustrated by embodiment 1 in FIGS. 1 and 2, a film material should be selected which is impermeable to the reactive medium of the environment. However, if the indicator is to be used as a steam sterilization indicator as in embodiment 2, FIGS. 3–5, then a film material which is permeable to water vapor must be used.

The chemical 7 which reacts with the wick may comprise any suitable indicator chemicals which are known to the art. Typical indicator chemicals include 2,4-Dinitrophenylhydrazones (DNP) which can be prepared in a wide range of melting points. Another suitable indicator chemical is salicylamide. A particularly preferred indicator compound which is relatively inexpensive and which has been found to be particularly effective is sebacic acid, also known as decanedioic acid (chemical formula $COOH-(CH_2)_8COOH$). If the chemical indicator material is colorless, a small amount of a coloring dye may be added to the indicator. The optional backing 8 is not critical, but may be preferred in certain applications. Polymeric materials and metal foils, such as aluminum, comprise suitable backing materials. The main requirement of the backing material is that it provide dimensional stability to the device and be inactive or resistant to the environment or process to which the device is exposed.

A preferred device suitable for use in steam sterilization is that of the type illustrated by FIGS. 3, 4 and 5. In one example of this device, the wick 2 is made of a filter paper available from Schleicher and Schuell, Inc. of Keene, N.H. under the name 591-A Filter Paper. Before heat sealing, a small amount of sebacic acid containing crystal violet blue dye is placed at one end of and in intimate contact with the wick. The wick and sebacic acid are then heat sealed in a polypropylene envelope. The bottom film of polypropylene is about 0.7 mils in thickness while the top film thickness is about 0.9 mils thick. This sealed envelope is bonded to an aluminum foil backing approximately 3 mils thick with a urethane adhesive available under the tradename Adcote 503H/Catalyst "F" from Morton Chemical Co., Chicago, Ill. The resulting structure is suitable for use as an indicator for steam sterilization. The time at which the device is maintained above a particular temperature is satisfactorily indicated by the progression of the colored zone of the sebacic acid along the wick.

Although particular embodiments of the present invention have been disclosed herein for purposes of explanation, further modifications or variations thereof will be apparent to those skilled in the art to which this invention pertains.

I claim:

1. An indicator device suitable for use in steam sterilization which comprises:
   a. an aluminum foil backing member;
   b. an indicator chemical which comprises sebacic acid which has the capability of wicking through a wick material;
   c. wicking means in the form of a length of filter paper with one end of said wicking means in physical contact with said indicator chemical;
   d. said indicator chemical and wicking means being contained within a water vapor permeable polypropylene envelope with the top and bottom interfaces of said envelope being sealed together to mechanically bond the wicking means and indicator chemical along the entire film envelope interfaces;
   e. with said envelope being mounted on said backing member.

2. An indicator device which is based upon the rate of an indicating chemical wicking through a wick material which comprises:
   a. an indicator chemical which comprises sebacic acid which has the capability of wicking through a wick material at a given predetermined temperature or temperature range;
   b. a wick material having one end of said wick material in contact with said indicator chemical;
   c. said indicator chemical and wick material being contained in a film envelope with top and bottom interfaces of said envelope being sealed together to mechanically bond the wick material at the film envelope interfaces.

3. An indicator device suitable for use in steam sterilization which comprises:
   a. a backing member;
   b. an indicator chemical which comprises sebacic acid which has the capability of wicking through a wick material;
   c. wicking means having one end of said wicking means in physical contact with said indicator chemical;
   d. said indicator chemical and wicking means being contained within a polypropylene envelope with the top and bottom interfaces of said envelope being sealed together to mechanically bond the wicking means and indicator chemical at the film envelope interfaces;
   e. with said envelope being mounted on said backing member.

4. An indicator device suitable for use in steam sterilization which comprises:
   a. a backing member;
   b. an indicator chemical which comprises sebacic acid which further contains a dye meterial and which has the capability of wicking through a wick material;
   c. wicking means having one end of said wicking means in physical contact with said indicator chemical;
   d. said indicator chemical and wicking means being contained within a polypropylene envelope with the top and bottom interfaces of said envelope being sealed together to mechanically bond the wicking means and indicator chemical at the film envelope interfaces;
   e. with said envelope being mounted on said backing member.

5. An indicator device which is based upon the rate of an indicating chemical wicking through a wick material which comprises:
   a. a solid indicator chemical having a defined melting point and which has the capability of wicking through a wick material at a given predetermined temperature or temperature range;
   b. a wick material having one end of said wick material in contact with said indicator chemical;
   c. said indicator chemical and wick material being contained in a film envelope with top and bottom interfaces of said envelope being sealed together to mechanically bond the wick material at the film envelope interfaces to prevent any significant flow of indicator chemical along the periphery of the wick during use.

* * * * *